United States Patent [19]
Nagai et al.

[11] Patent Number: 6,143,150
[45] Date of Patent: Nov. 7, 2000

[54] BIOLOGICAL GAS SENSOR

[75] Inventors: Yuko Nagai; Tetsushi Sekiguchi; Michihiro Nakamura; Kohei Ono, all of Tokyo, Japan

[73] Assignee: Nihon Kohden Corporation, Tokyo, Japan

[21] Appl. No.: 08/887,631

[22] Filed: Jul. 3, 1997

[30] Foreign Application Priority Data

| Jul. 3, 1996 | [JP] | Japan | 8-173699 |
| May 28, 1997 | [JP] | Japan | 9-138196 |

[51] Int. Cl.[7] ................................ G01N 27/26
[52] U.S. Cl. .................. 204/431; 204/403; 204/415
[58] Field of Search .................. 204/403, 415, 204/416, 418, 431; 205/782.5, 783, 785.5, 789; 73/23.2, 23.3, 31, 31.02; 600/311, 348, 353; 436/167, 68, 62; 422/84, 86, 88, 90

[56] References Cited

U.S. PATENT DOCUMENTS

| 3,932,583 | 1/1976 | Schievelbein | 423/232 |
| 3,988,233 | 10/1976 | Gamer et al. | 204/415 |
| 4,141,800 | 2/1979 | Bruer et al. | 205/779.5 |
| 4,218,298 | 8/1980 | Shimada et al. | 204/195 |
| 4,460,451 | 7/1984 | Inoue et al. | 204/415 |
| 4,474,183 | 10/1984 | Yano et al. | 128/635 |
| 4,643,192 | 2/1987 | Fiddian-Green | 128/632 |
| 5,071,526 | 12/1991 | Pletcher et al. | 205/782.5 |
| 5,179,002 | 1/1993 | Fehder | 435/25 |
| 5,212,092 | 5/1993 | Jackson et al. | 436/11 |

FOREIGN PATENT DOCUMENTS

| 0 102 033 | 3/1984 | European Pat. Off. |
| 0 355 896 | 2/1990 | European Pat. Off. |
| 0 572 156 | 12/1993 | European Pat. Off. |
| 61-144562 | 7/1986 | Japan | G01N 27/30 |
| 7-231885 | 9/1995 | Japan | A61B 5/14 |

*Primary Examiner*—T. Tung
*Assistant Examiner*—Alex Noguerola
*Attorney, Agent, or Firm*—Sughrue, Mion, Zinn, Macpeak & Seas, PLLC

[57] ABSTRACT

A biological gas sensor for measuring a carbon dioxide partial pressure in an alimentary canal while excluding the influences of hydrogen sulfide and/or weak acid is disclosed. The gas sensor comprises a sensor which has in the sensitive part thereof a bicarbonate buffer solution held by a gas permeable membrane and detects a carbon dioxide partial pressure based on the hydrogen ion concentration of the bicarbonate buffer solution, a liquid holding part which is formed of a gas permeable tube having in the inside thereof the sensitive part of the sensor, an isotonic solution which is held in the liquid holding part and is isotonic with the bicarbonate buffer solution, and a metallic member (e.g., a coil of copper wire) so that hydrogen sulfide entering the liquid holding part may react with the metal and precipitate.

17 Claims, 9 Drawing Sheets

BIOLOGICAL GAS SENSOR

FIELD OF THE INVENTION

This invention relates to an improved biological gas sensor for measuring a carbon dioxide partial pressure in an alimentary canal, mainly the esophagus and the gastrointestinal tube.

BACKGROUND OF THE INVENTION

In case a circulating blood flow decreases by some cause in, for example, a patient in intensive care unit (ICU), the blood that has been supplied to the organs in the abdominal cavity is redistributed to the other important organs. As a result, the blood flow in the mucous membrane of the alimentary canal begins to decrease earlier than the other organs to fall into hypoperfusion. It follows that the mucous membrane falls into hypoxemia, which leads to acidosis of the tissue. The mucous tissue is then destroyed to allow colonic bacteria or endotoxin into the body fluids, causing sepsis or multiple organ failure. That is, early finding and early treatment of hypoperfusion in the alimentary canal could remove one of the causes of multiple organ failure, which is said to be a main cause of death in ICU. In order to detect an increase in carbon dioxide partial pressure due to hypoperfusion, a sensor for a carbon dioxide partial pressure in an alimentary canal has been proposed, which is to be fitted to the tip of a stomach tube or an ileus tube inserted into the alimentary canal for medical treatment, as disclosed in JP-A-7-231885 (the term "JP-A" as used herein means an "unexamined published Japanese patent application"). The carbon dioxide gas sensor to be used includes the one described in JP-A-61-144562, which detects the concentration of carbon dioxide dissolved in a bicarbonate buffer solution (e.g., $NaHCO_3$ solution) as a change in hydrogen ion concentration by means of an Ion-Sensitive Field-Effect Transistor (ISFET).

However, the conventional biological gas sensor of this type tends to indicate a higher level than the actual carbon dioxide partial pressure, failing to make accurate measurement, because the hydrogen ion concentration of a bicarbonate buffer solution contained in the sensitive part is liable to increase in the presence of hydrogen sulfide gas or compounds thereof and/or weak acids or gas thereof which exist in the alimentary canal.

SUMMARY OF THE INVENTION

An object of the present invention is to provide a biological gas sensor with which a carbon dioxide partial pressure in an alimentary canal can be measured accurately without being affected by the presence of hydrogen sulfide gas or compounds thereof and/or weak acids or gas thereof.

The present invention provides a biological gas sensor comprising a sensor which has in the sensitive part thereof a bicarbonate buffer solution held by a gas permeable membrane and detects a carbon dioxide partial pressure based on the hydrogen ion concentration of the bicarbonate buffer solution, a liquid holding part which has in the inside thereof the sensitive part of the sensor and at least a part of the inner wall thereof is made of a gas permeable membrane, an aqueous solution which is held in the liquid holding part and is substantially isotonic with the bicarbonate buffer solution, and a metallic member which is in the liquid holding part and is reactive with hydrogen sulfide.

In a preferred embodiment of the above-described gas sensor, the metallic member is a coil, a cylinder with perforations or a cylinder made of a net, through which the sensor is inserted.

The present invention also provides a biological gas sensor comprising a sensor which has in the sensitive part thereof a bicarbonate buffer solution held by a gas permeable membrane and detects a carbon dioxide partial pressure based on the hydrogen ion concentration of the bicarbonate buffer solution, a liquid holding part which has in the inside thereof the sensitive part of the sensor and at least a part of the inner wall thereof is made of a gas permeable membrane, and an aqueous solution which is held in the liquid holding part, is substantially isotonic with the bicarbonate buffer solution, and contains a metallic ion or a metallic compound capable of reacting with hydrogen sulfide.

The present invention further provides a biological gas sensor comprising a sensor which has in the sensitive part thereof a bicarbonate buffer solution held by a gas permeable membrane and detects a carbon dioxide partial pressure based on the hydrogen ion concentration of the bicarbonate buffer solution, a liquid holding part which has in the inside thereof the sensitive part of the sensor and at least a part of the inner wall thereof is made of a gas permeable membrane containing powder of a metal or a compound thereof capable of reacting with hydrogen sulfide, and an aqueous solution which is contained in the liquid holding part and is substantially isotonic with the bicarbonate buffer solution.

The present invention furthermore provides a biological gas sensor comprising a sensor which has in the sensitive part thereof a bicarbonate buffer solution held by a gas permeable membrane and detects a carbon dioxide partial pressure based on the hydrogen ion concentration of the bicarbonate buffer solution, wherein the gas permeable membrane contains powder of a metal or a compound thereof capable of reacting with hydrogen sulfide.

In a preferred embodiment of the above-described gas sensors, the metal is selected from the group consisting of copper, silver, cobalt, nickel, iron, manganese, and molybdenum.

The present invention furthermost provides a biological gas sensor comprising a sensor which has in the sensitive part thereof a bicarbonate buffer solution held by a gas permeable membrane and detects a carbon dioxide partial pressure based on the hydrogen ion concentration of the bicarbonate buffer solution, a liquid holding part which has in the inside thereof the sensitive part of the sensor and at least a part of the inner wall thereof is made of a gas permeable membrane, and an aqueous alkaline solution which is contained in the liquid holding part and is substantially isotonic with the bicarbonate buffer solution.

In a preferred embodiment of the above gas sensor, the gas sensor has a means for allowing carbon dioxide gas into the bicarbonate buffer solution in the sensitive part thereof while preventing hydrogen sulfide or compound gases thereof from reaching the bicarbonate buffer solution. This means is preferably a gas permeable membrane containing powder of a metal or a compound thereof capable of reacting with hydrogen sulfide, which is used for holding the bicarbonate buffer solution of the sensitive part.

DETAILED DESCRIPTION OF THE INVENTION

Figure 1:
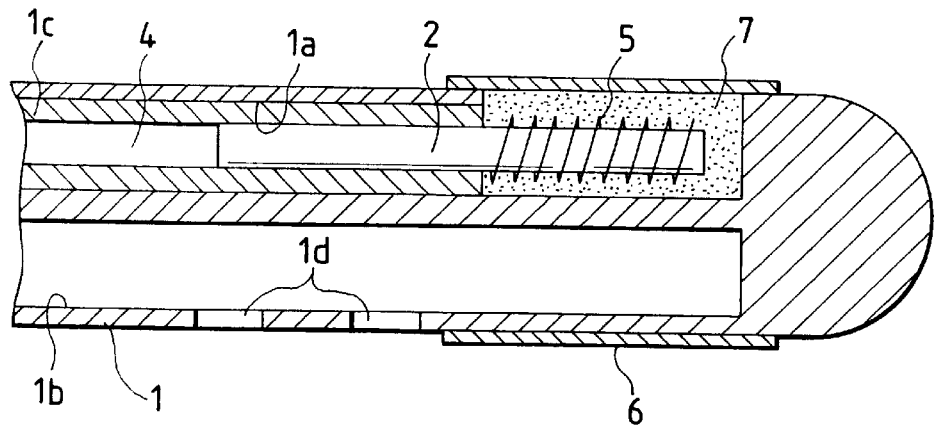
FIG. 1 shows a first embodiment of the gas sensor according to the present invention.
Figure 2:
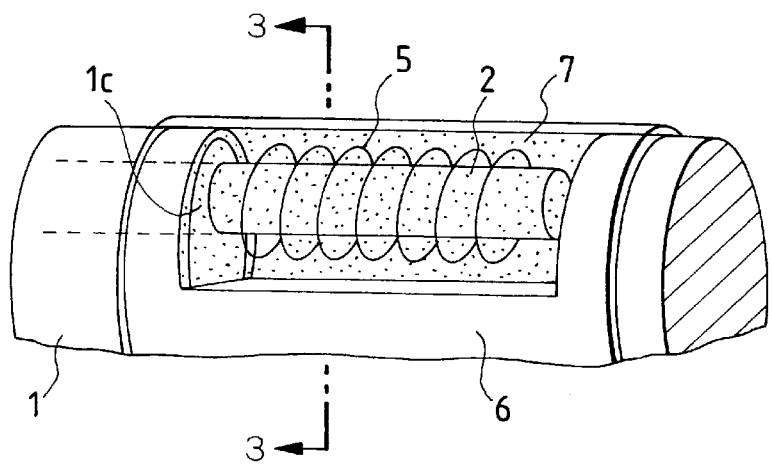
FIG. 2 shows a principal part of the gas sensor of FIG. 1.

FIG. 1 shows the whole structure of the first embodiment of the gas sensor according to the present invention. In FIG. 2 is shown the principal part of the gas sensor of FIG. 1, the cross section of which along 3—3 line is shown in FIG. 3.

Figure 3:
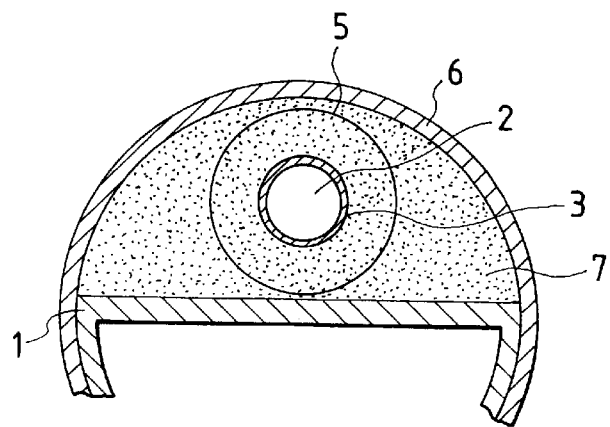
FIG. 3 is a cross section along 3—3 line shown in FIG. 2.

As shown in FIGS. 1 through 3, sensor 2 is set in one of the lumens (lumen 1a) provided near the tip of double lumen catheter 1 made of silicone. Sensor 2 is of the type disclosed in JP-A-61-144562, being composed of ISFET, a bicarbonate buffer solution, and a gas permeable membrane. The surface of the sensitive part of sensor 2 is intimately covered with silicone-made gas permeable membrane 3 (see FIG. 3). Double lumen catheter 1 has a hemispherical shape at the tip, and the two lumens 1a and 1b each have a closed end at the side of the tip. To sensor 2 is connected one end of lead 4 (see FIG. 1) which is also inserted in lumen 1a, with the other end thereof connected to a measuring instrument externally provided.

Part of the wall on the side of lumen 1a is cut away to make an opening near the tip of catheter 1 so that the sensitive part of sensor 2 is exposed to the outer environment through the opening. The space between sensor 2 and lead 4 and the inner wall of lumen 1a is filled with silicone resin 1c. A coil of copper wire 5 is put over the sensitive part of sensor 2 with a certain gap therebetween. Gas permeable tube 6 made of silicone is fitted around the periphery of double lumen catheter 1 so as to cover the opening. Tube 6 and the outer wall of double lumen catheter 1 are tightly adhered with a silicone, and there is formed a closed space at the cut-away part of lumen 1a which serves as a liquid holding part. The liquid holding part, in which the sensitive part of sensor 2 is exposed, is filled with isotonic liquid 7, such as physiological saline, that is isotonic with the electrode internal liquid of sensor 2, i.e., a bicarbonate buffer solution.

The inside of lumen 1b is open to the outer environment through a plurality of openings 1d provided in a single line in the longitudinal direction in the vicinity of the tip of double lumen catheter 1. Lumen 1b is for discharging secreting fluid from an alimentary canal or for supplying liquid to an alimentary canal for lavage and the like.

Figure 4:
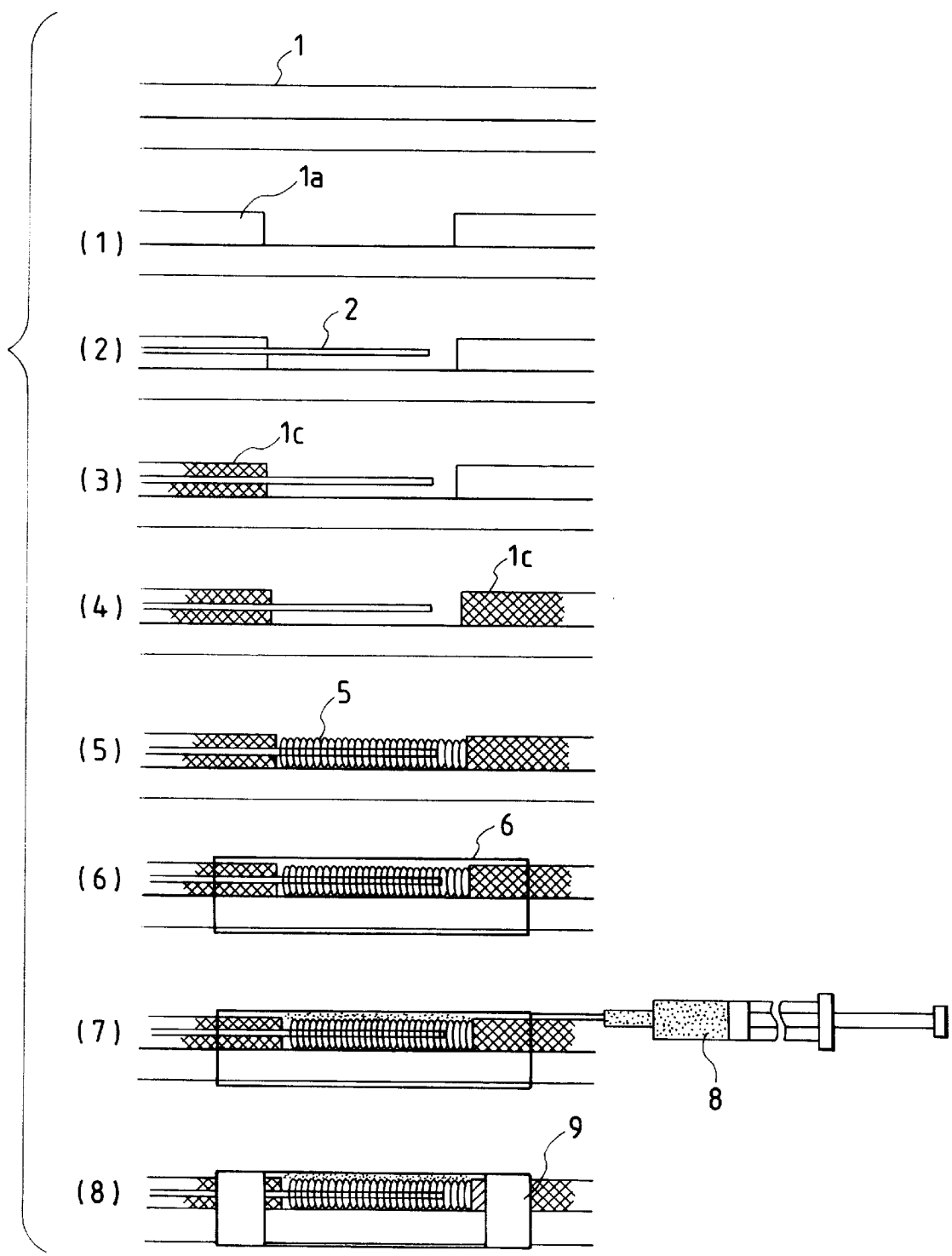
FIG. 4 illustrates the steps of producing the gas sensor according to the first embodiment.

Part of the steps for producing the biological gas sensor of the first embodiment are shown in FIG. 4. Included are a step of setting sensor 2 in silicone-made double lumen catheter 1, a step of providing copper wire 5 in a coil around sensor 2, a step of forming a liquid holding part, and a step of filling the liquid holding part with isotonic liquid 7. In more detail, these steps are carried out as follows.

(1) The wall of silicone-made double lumen catheter 1 on the side of lumen 1a is cut off over a length of 3 cm in the longitudinal direction and over the whole width of lumen 1a.

(2) Sensor 2 is inserted through lumen 1a so as to be positioned at the center of the cut-away portion.

(3) Silicone resin 1c is injected into the root of sensor 2 to fix sensor 2 in double lumen catheter 1.

(4) Silicone resin 1c is also injected into the other side of lumen 1a (the tip side) to clog lumen 1a.

(5) Copper wire 5 in a coil having a length of 3 cm is put over sensor 2.

(6) Silicone-made gas permeable tube 6 having a length of 5 cm whose inner diameter is equal to the outer diameter of double lumen catheter 1 is swollen with n-hexane as an organic solvent and then fitted on double lumen catheter 1 to cover the opening thereby forming a liquid holding part. On allowing tube 6 to stand, n-hexane vaporizes to achieve shrink-fit.

(7) Physiological saline is injected into the liquid holding part through between tube 6 and double lumen catheter 1 by means of syringe 8.

(8) The gap between double lumen catheter 1 and both ends of tube 6 are filled with silicone resin 9 to adhere them.

When the biological gas sensor having the above-described structure is inserted into the alimentary canal of a patient, carbon dioxide gas and hydrogen sulfide gas present in the outside fluid pass through gas permeable tube 6 and reach isotonic liquid 7, where hydrogen sulfide gas reacts with copper wire 5 and a copper ion (Cu++) dissolved therefrom as represented by reaction formula:

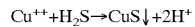

$$Cu^{++} + H_2S \rightarrow CuS\downarrow + 2H^+$$

As a result, hydrogen sulfide gas precipitates as copper sulfide in isotonic solution 7 and cannot pass through gas permeable membrane 3 on the surface of the sensitive part of sensor 2. Thus, hydrogen sulfide gas is selectively removed, whereas only carbon dioxide gas reaches the sensitive part of sensor 2.

In order to demonstrate the mechanism of action of the gas sensor according to the present invention, an experiment was carried out as follows. Each of the gas sensor according to the first embodiment of the present invention and a conventional biological gas sensor having no copper wire was calibrated with a standard solution having a carbon dioxide partial pressure of 36 mmHg or 84 mmHg. The thus calibrated gas sensor was immersed in a 20 ppm hydrogen sulfide aqueous solution for 1 hour and then immersed in the same standard solution as used above. The values indicated by the gas sensors are shown in Table 1 below.

TABLE 1

| | $CO_2$ Partial Pressure (mmHg) | |
|---|---|---|
| Standard Solution | 36 | 84 |
| Conventional Sensor | 112 | 250 |
| Sensor of the Invention | 38 | 85 |

As can be seen from Table 1, the biological gas sensor of the present invention accurately detects a carbon dioxide partial pressure without being affected by hydrogen sulfide gas compared with the conventional biological gas sensor.

Figure 5:
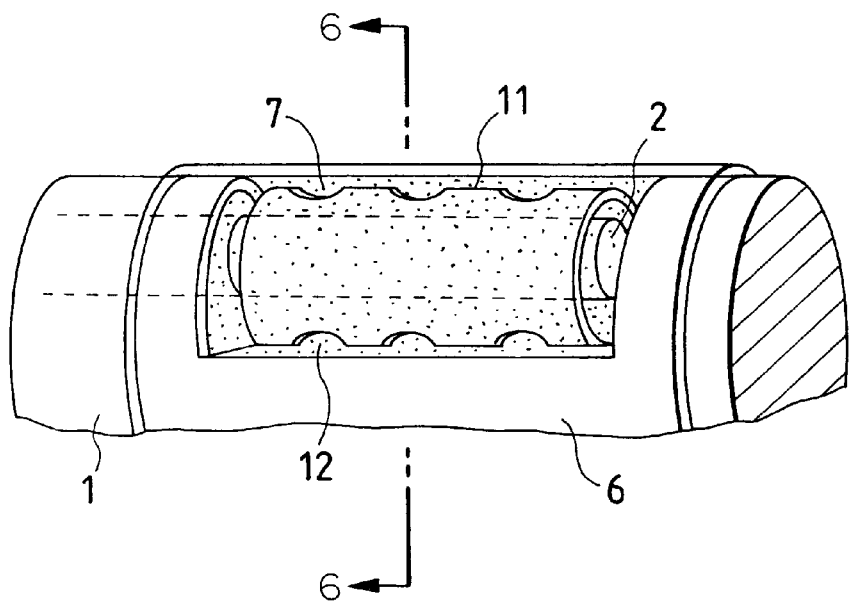
FIG. 5 shows a principal part of a second embodiment of the gas sensor according to the present invention.
Figure 6:
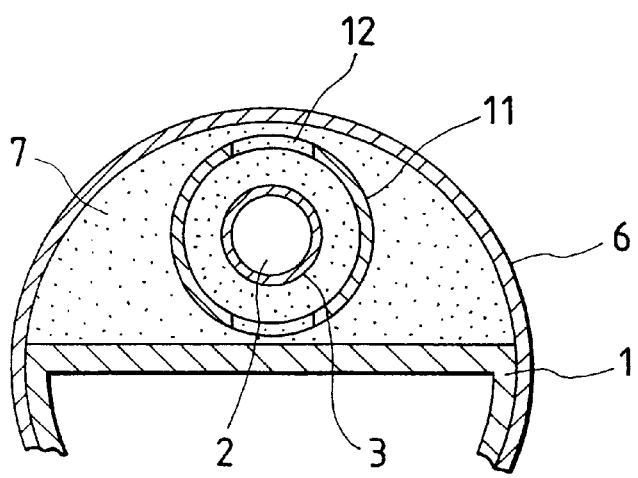
FIG. 6 is a cross section along 6—6 line shown in FIG. 5.

A second embodiment of the present invention are shown in FIGS. 5 and 6. FIG. 5 illustrates the principal part, and FIG. 6 is a cross section along line 6—6 of FIG. 5. The only difference of the second embodiment from the first one resides in that copper wire 5 in a coil of the first embodiment is replaced with perforated cylinder 11 made of copper. Cylinder 11 has a plurality of perforations 12 in pair (three pairs in FIG. 5), each pair facing to each other. The other constituent elements are the same as those in the first embodiment. The action and effect produced by such a structure are equal to those obtained by the first embodiment.

Figure 7:
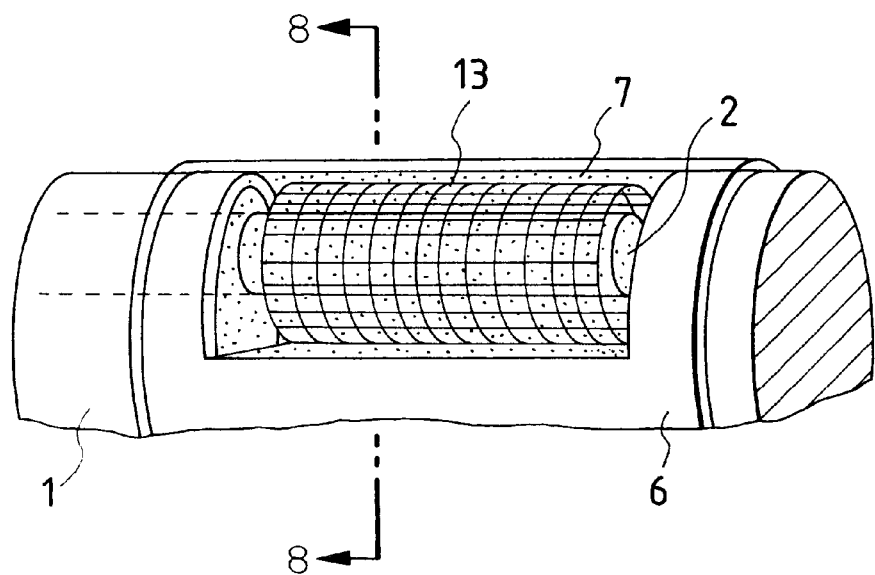
FIG. 7 shows a principal part of a third embodiment of the gas sensor according to the present invention.
Figure 8:
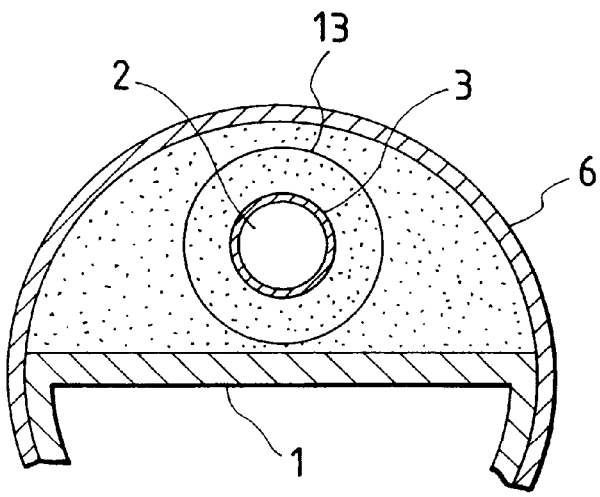
FIG. 8 is a cross section along 8—8 line shown in FIG. 7.

FIGS. 7 and 8 illustrate a third embodiment of the present invention. FIG. 7 shows the principal part, and FIG. 8 is a cross section along line 8—8 of FIG. 7. The difference of the third embodiment from the first one consists in that copper wire 5 in a coil of the first embodiment is replaced with cylinder 13 made of a copper net. The other constituent elements are the same as those in the first embodiment. The action and effect produced by such a structure are equal to those obtained by the first embodiment.

Figure 9:
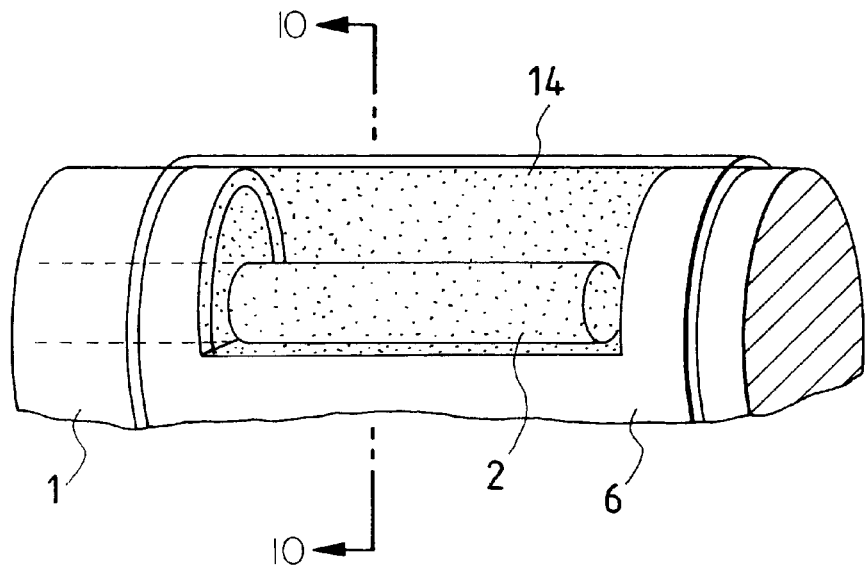
FIG. 9 shows a principal part of a fourth embodiment of the gas sensor according to the present invention.
Figure 10:
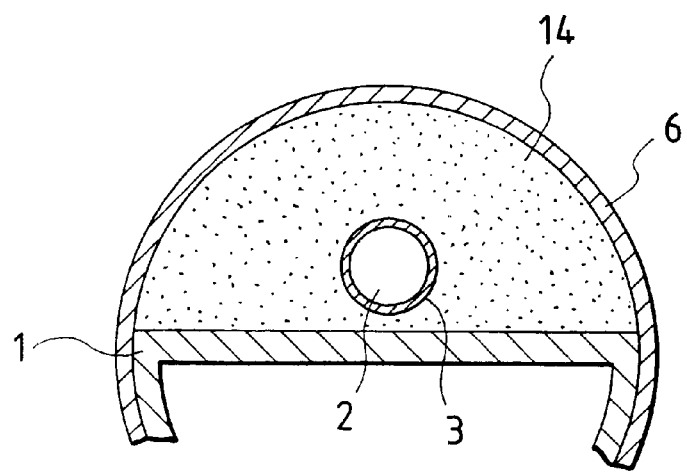
FIG. 10 is a cross section along 10—10 line shown in FIG. 9.

FIGS. 9 and 10 show a fourth embodiment of the present invention. FIG. 9 shows the principal part, and FIG. 10 is a cross section along line 10—10 of FIG. 9. In this embodiment, copper wire 5 of the first embodiment is not used, and isotonic liquid 7 (e.g., saline) as used in the first embodiment is replaced with isotonic liquid 14 containing a copper compound. The other constituent elements are the same as those in the first embodiment. The action and effect produced by such a structure are equal to those obtained by the first embodiment.

Figure 11:
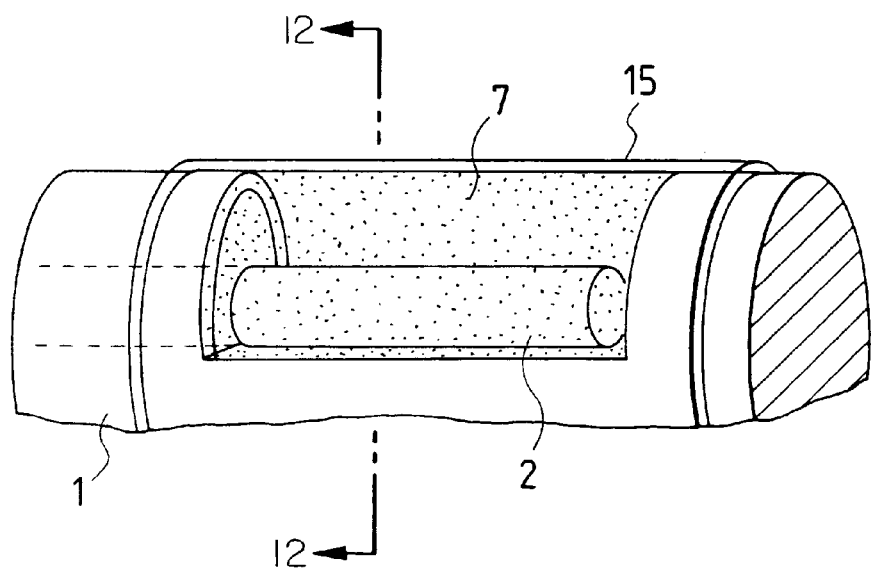
FIG. 11 shows a principal part of a fifth embodiment of the gas sensor according to the present invention.
Figure 12:
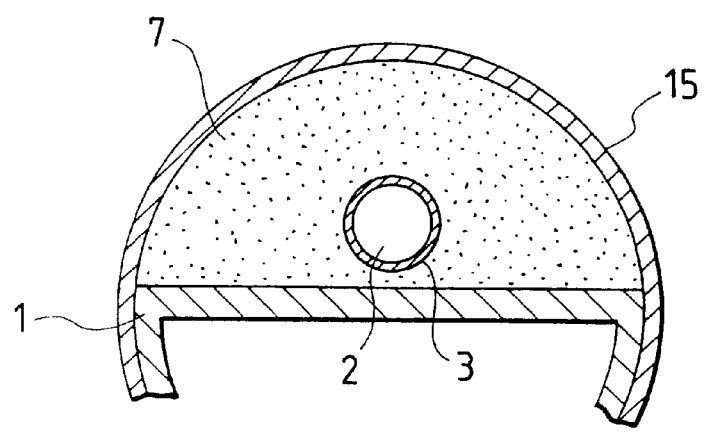
FIG. 12 is a cross section along 12—12 line shown in FIG. 11.

FIGS. 11 and 12 show a fifth embodiment of the present invention. FIG. 11 shows the principal part, and FIG. 12 is a cross section along line 12—12 of FIG. 11. In this embodiment, copper wire 5 of the first embodiment is not used, and, instead, silicone-made tube 6 as used in the first embodiment is replaced with gas permeable tube 15 made of silicone containing copper powder. The other constituent elements are the same as those in the first embodiment. According to this structure, hydrogen sulfide gas undergoes reaction with copper on the outer and inner surfaces of tube 15 and settled thereon as copper sulfide. Therefore, hydrogen sulfide cannot reach the inside isotonic liquid 7, whereby the same action and effect as observed in the first embodiment result.

Figure 13:
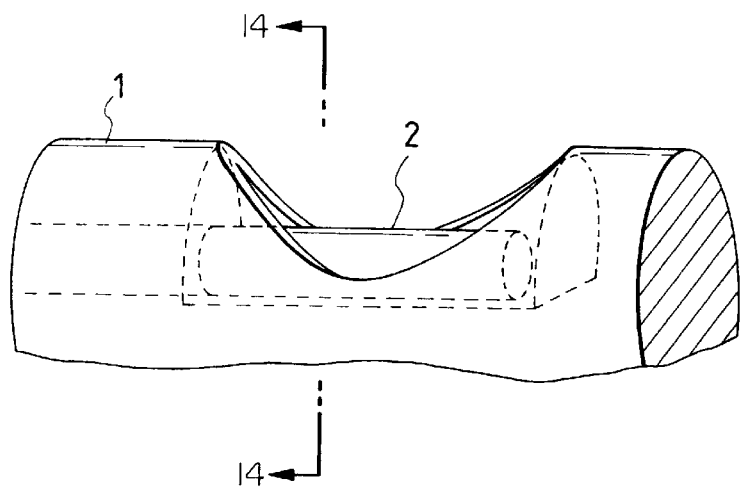
FIG. 13 shows a principal part of a sixth embodiment of the gas sensor according to the present invention.
Figure 14:
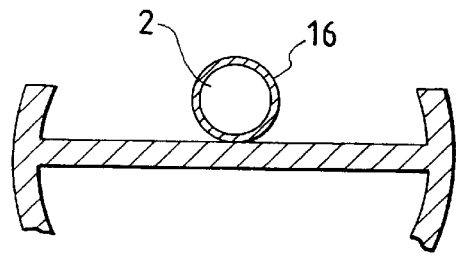
FIG. 14 is a cross section along 14—14 line shown in FIG. 13.

FIGS. 13 and 14 show a sixth embodiment of the present invention. FIG. 13 shows the principal part, and FIG. 14 is a cross section along line 14—14 of FIG. 13. This embodiment does not have copper wire 5, tube 6, and isotonic liquid 7 used in the first embodiment, but, instead, silicone-made gas permeable membrane 3 as used in the first embodiment is replaced with gas permeable membrane 16 which is made of silicone containing copper powder. Further, while in the first embodiment the cuts made at both ends of the opening of the wall of lumen 1a at the side of the root of sensor 2 and the side nearer to the tip of the double lumen catheter 1 are both perpendicular to the partition between lumen 1a and lumen 1b, in the sixth embodiment the cuts are diagonal to the partition in such a manner that the area of the remaining wall covering the sensitive part of sensor 2 gradually increases from the center of the sensitive part toward the root and the tip thereof. Such a way of cutting is for protection of the sensitive part of sensor 2. The other constituent elements are the same as those in the first embodiment. According to this structure, hydrogen sulfide gas undergoes reaction with copper on the outer and inner surfaces of gas permeable member 16 and settled thereon as copper sulfide. Therefore, hydrogen sulfide cannot reach the inside bicarbonate buffer solution whereby the same action and effect as obtained in the first embodiment result.

While in the foregoing embodiments copper is used as a metal reactive with hydrogen sulfide, other metals capable of reacting with hydrogen sulfide produce the same effect. Taking safety to the human body and ease of production into consideration, silver, cobalt, nickel, iron, manganese, and molybdenum are suitable in addition to copper. The reactions between these metals and hydrogen sulfide are represented by the following formulae:

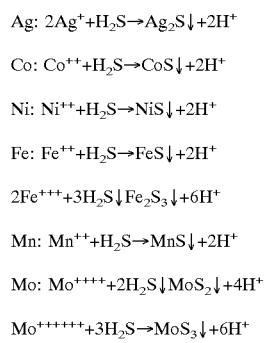

Ag: $2Ag^+ + H_2S \rightarrow Ag_2S\downarrow + 2H^+$

Co: $Co^{++} + H_2S \rightarrow CoS\downarrow + 2H^+$

Ni: $Ni^{++} + H_2S \rightarrow NiS\downarrow + 2H^+$

Fe: $Fe^{++} + H_2S \rightarrow FeS\downarrow + 2H^+$ $2Fe^{+++} + 3H_2S \downarrow Fe_2S_3 \downarrow + 6H^+$ Mn: $Mn^{++} + H_2S \rightarrow MnS\downarrow + 2H^+$ Mo: $Mo^{++++} + 2H_2S \downarrow MoS_2 \downarrow + 4H^+$ $Mo^{++++++} + 3H_2S \rightarrow MoS_3 \downarrow + 6H^+$ Of these metals, those suited to the first to third embodiments are copper, silver, nickel, iron, and molybdenum.

Metallic compounds which can be used in preparing an isotonic liquid practical for the fourth embodiment, i.e., an aqueous solution containing a metal ion include $AgClO_4$, $AgF$, $AgNO_3$, $CuBr_2$, $CuCl_2$, $Cu(NO_3)_2$, $CuSO_4$, $CuC_2O_4$, $FeBr_2$, $FeCl_2$, $FeCl_3$, $Fe(ClO_4)_2$, $Fe(ClO_4)_3$, $Fe(NO_3)_2$, $Fe(NO_3)_3$, $NiBr_2$, $NiCl_2$, $Ni(ClO_4)_2$, $NiI_2$, $Ni(NO_3)_2$, $NiSO_4$, $(NH_4)_2MoO_4$, $CoBr_2$, $COCl_2$, $CoI_2$, $Co(NO_3)_2$, $CoSO_4$, $MnBr_2$, $MnCl_2$, $Mn(NO_3)_2$, and $MnSO_4$.

Metal powder useful in the fifth and sixth embodiments in addition to copper powder includes powder of $CuO$, $Cu_2O$, $Ag$, $Ag_2O$, $Co$, $CoO$, $Co_2O_3$, $CO_3O_4$, $Ni$, $NiO$, $Fe$, $FeO$, $Fe_2O_3$, $Mn$, $MnO_2$, $Mo$, and $MoO_3$.

Figure 15:
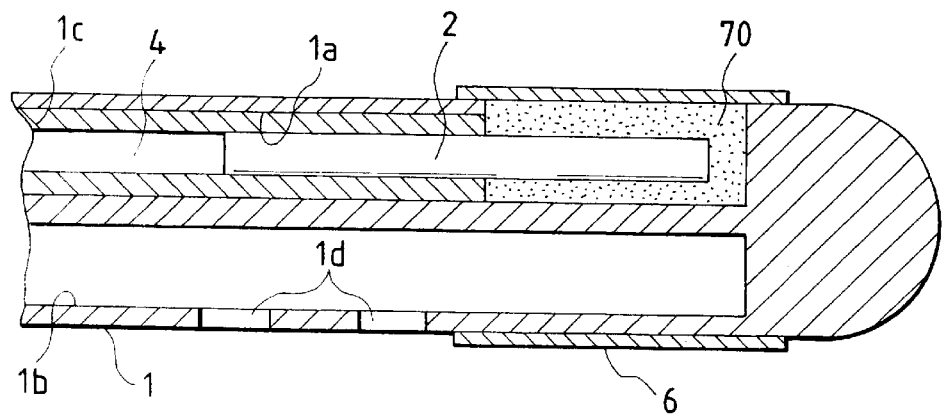
FIG. 15 shows a seventh embodiment of the gas sensor according to the present invention.
Figure 16:
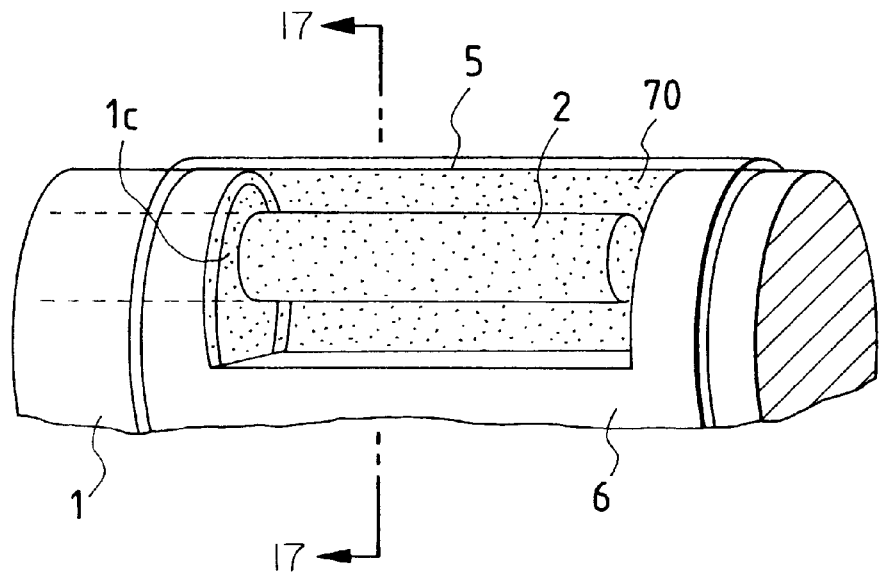
FIG. 16 shows a principal part of the gas sensor of FIG. 15.
Figure 17:
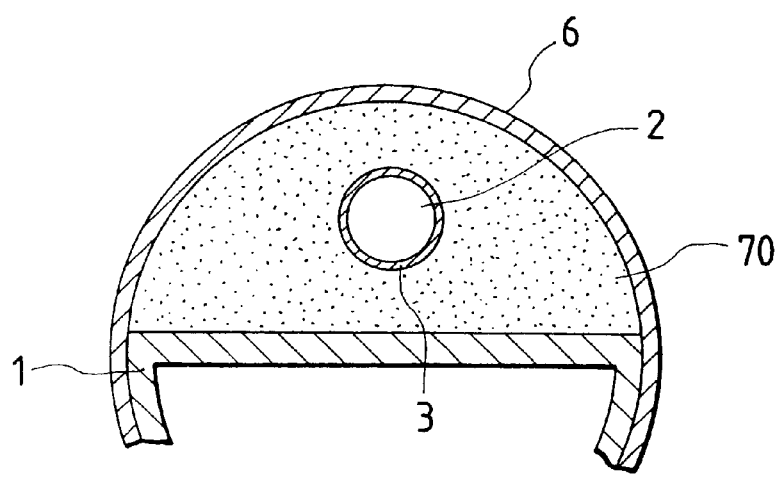
FIG. 17 is a cross section along 17—17 line shown in FIG. 16.

FIGS. 15 through 17 show a seventh embodiment of the present invention. FIG. 15 illustrates the whole structure of this embodiment, FIG. 16 shows the principal part thereof, and FIG. 17 is a cross section along line 17—17 of FIG. 16. As shown in FIGS. 15 to 17, the difference of this embodiment from the first one is that copper wire 5 is not used and isotonic liquid 7, such as physiological saline, is replaced with an aqueous alkaline solution 70 which is isotonic with the bicarbonate buffer solution of sensor 2. The other constituent elements are the same as those in the first embodiment.

When the biological gas sensor according to the seventh embodiment is inserted into the alimentary canal of a patient, carbon dioxide gas and weak acids or gaseous molecules thereof pass through gas permeable tube 6 and reach aqueous alkaline solution 70, where a weak acid (HA) ionizes as follows by the action of the aqueous alkaline solution.

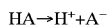

The weak acid and/or gas thereof in their molecular state HA pass through gas permeable membrane 3 on the surface of the sensitive part of sensor 2 but, on ionization in aqueous alkaline solution 70, they cannot pass any more. For example, acetic acid, which is present in gastric juice at a concentration of several hundreds of ppm, hardly ionizes in a common aqueous solution (gastric juice) because of its weak acidity and exists substantially in its molecular state as follows.

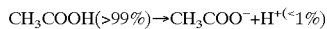

In this case, molecular acetic acid $CH_3COOH$ passes through gas permeable membrane 3 on the surface of the sensitive part of sensor 2 to give adverse influence to sensor 2. On the other hand, if acetic acid reacts with an aqueous alkaline solution, it ionizes almost 100% as follows and no more passes through gas permeable membrane 3, giving no adverse influence to sensor 2.

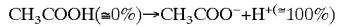

Like this, weak acids or gaseous molecules thereof can be removed selectively by aqueous alkaline solution 70, and only carbon dioxide gas reaches the sensitive part of sensor 2.

In order to demonstrate the mechanism of action of the gas sensor according to the seventh embodiment, an experiment was carried out as follows. Each of the gas sensor according to the seventh embodiment and a conventional biological gas sensor having neither a copper wire nor an aqueous alkaline solution was calibrated with a standard solution having a carbon dioxide partial pressure of 35 mmHg or 84 mmHg. The thus calibrated gas sensor was immersed in 0.2% acetic acid for 21 hours at 37° C. and then immersed in the same standard solution as used above. The values indicated by the gas sensors are shown in Table 2 below. In this case, further, 100 mM-$NaHCO_3$ aqueous solution was used as the aqueous alkaline solution for the gas sensor of the present invention.

TABLE 2

|  | $CO_2$ Partial Pressure (mmHg) | |
| --- | --- | --- |
| Standard Solution | 35 | 84 |
| Conventional Sensor | 53 | 130 |
| Sensor of the Invention | 33 | 84 |

It is seen from Table 2 that the biological gas sensor of the present invention accurately detects a carbon dioxide partial pressure without being affected by acetic acid compared with the conventional biological gas sensor.

The pH of the aqueous alkaline solution to be used in the gas sensor and the pKa value of a weak acid to be eliminated by the aqueous alkaline solution should satisfy relationship:

[pKa of weak acid]<[pH of aqueous alkaline solution]

preferably, pKa+3<pH.

Figure 18:
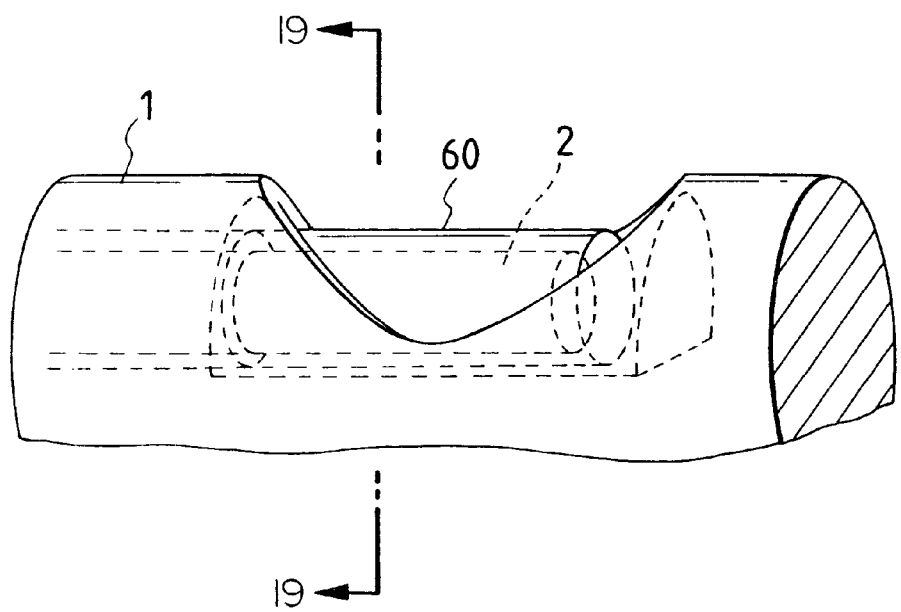
FIG. 18 shows a principal part of an eighth embodiment of the gas sensor according to the present invention.
Figure 19:
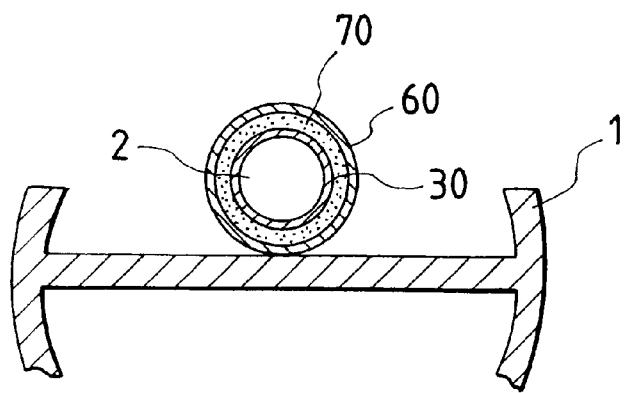
FIG. 19 is a cross section along 19—19 line shown in FIG. 18.

FIGS. 18 and 19 show an eighth embodiment of the present invention. FIG. 18 illustrates the principal part of the gas sensor, and FIG. 19 is a cross section along line 19—19 of FIG. 18. The difference of this embodiment from the seventh one is that gas permeable tube 6 used in the seventh embodiment is not used and, instead, gas permeable tube 60 is concentrically provided around the sensitive part of sensor 2 to make a space between gas permeable membrane 3 and gas permeable tube 60, into which aqueous alkaline solution 70 isotonic with the bicarbonate buffer solution in sensor 2 is injected, and gas permeable membrane 3 used here is gas permeable membrane 30 made of silicone containing copper oxide. The shape of the cut made in the wall of lumen 1a is the same as in the sixth embodiment for protection of the sensitive part of sensor 2. The other constituent elements are the same as those in the seventh embodiment.

When carbon dioxide to be detected is present in the alimentary canal together with weak acids or gas thereof and hydrogen sulfide gas or compounds thereof, the weak acids or gas thereof are excluded by aqueous alkaline solution 70 through the same mechanism as in the seventh embodiment, and hydrogen sulfide gas or its compounds can be eliminated by gas permeable membrane 30 through the same mechanism as in the sixth embodiment. In other words, the gas sensor according to this embodiment combines the function of removing weak acids or gas thereof and the function of removing hydrogen sulfide gas or compounds thereof.

All the above-mentioned embodiments use a double lumen catheter as a means in which the gas sensor is set. This is advantageous in that carbon dioxide measurement with the gas sensor and discharge of secreting fluid from the alimentary canal or lavage of the alimentary canal can be effected simultaneously.

While ISFET is used as a sensor in the foregoing embodiments, similar action and effect can be obtained by using other sensitive systems for detecting a carbon dioxide partial pressure from changes of hydrogen ion concentration in a bicarbonate buffer solution, such as a Severinghause type electrode using a glass electrode and an optical fiber electrode coated with $NaHCO_3$ and a pH indicator dye as disclosed in JP-A-3-85430.

While silicone is used as a material of the double lumen catheter in the foregoing embodiments, other materials used in commercially available general catheters, such as polyvinyl chloride, can be used as well.

As described above, the present invention makes it possible to accurately measure a carbon dioxide partial pressure in an alimentary canal while excluding the influences of hydrogen sulfide gas or compounds thereof and/or weak acids or gas thereof that may coexist in the alimentary canal.

While the invention has been described in detail and with reference to specific examples thereof, it will be apparent to one skilled in the art that various changes and modifications can be made therein without departing from the spirit and scope thereof.

What is claimed is:

1. A biological gas sensor comprising:

a sensor which has in the sensitive part thereof a bicarbonate buffer solution held by a first gas permeable membrane and detects a carbon dioxide partial pressure based on the hydrogen ion concentration of the bicarbonate buffer solution;

a liquid holding part which has in the inside thereof the sensitive part of said sensor and at least a part of the inner wall of said holding part is made of a second gas permeable membrane;

an aqueous solution which is held in said liquid holding part and is substantially isotonic with said bicarbonate buffer solution; and a metallic member which is in said liquid holding part and is reactive with hydrogen sulfide.

2. A biological gas sensor according to claim 1, wherein said metallic member is a coil through which said sensor is inserted.

3. A biological gas sensor according to claim 2, wherein said metal is selected from the group consisting of copper, silver, cobalt, nickel, iron, manganese, and molybdenum.

4. A biological gas sensor according to claim 1, wherein said metallic member is a perforated cylinder through which said sensor is inserted.

5. A biological gas sensor according to claim 4, wherein said metal is selected from the group consisting of copper, silver, cobalt, nickel, iron, manganese, and molybdenum.

6. A biological gas sensor according to claim 1, wherein said metallic member is a cylinder made of a net through which said sensor is inserted.

7. A biological gas sensor according to claim 6, wherein said metal is selected from the group consisting of copper, silver, cobalt, nickel, iron, manganese, and molybdenum.

8. A biological gas sensor according to claim 1, wherein said metal is selected from the group consisting of copper, silver, cobalt, nickel, iron, manganese, and molybdenum.

9. A biological gas sensor comprising:
a sensor which has in the sensitive part thereof a bicarbonate buffer solution held by a first gas permeable membrane and detects a carbon dioxide partial pressure based on the hydrogen ion concentration of the bicarbonate buffer solution;
a liquid holding part which has in the inside thereof the sensitive part of said sensor and at least a part of the inner wall of said holding part is made of a second gas permeable membrane; and
an aqueous solution which is held in said liquid holding part, is substantially isotonic with said bicarbonate buffer solution, and contains a metallic ion or a metallic compound capable of reacting with hydrogen sulfide.

10. A biological gas sensor according to claim 9, wherein said metal is selected from the group consisting of copper, silver, cobalt, nickel, iron, manganese, and molybdenum.

11. A biological gas sensor comprising:
a sensor which has in the sensitive part thereof a bicarbonate buffer solution held by a first gas permeable membrane and detects a carbon dioxide partial pressure based on the hydrogen ion concentration of the bicarbonate buffer solution;
a liquid holding part which has in the inside thereof the sensitive part of said sensor and at least a part of the inner wall of said holding part is made of a second gas permeable membrane containing powder of a metal or a compound thereof capable of reacting with hydrogen sulfide; and
an aqueous solution which is contained in said liquid holding part and is substantially isotonic with said bicarbonate buffer solution.

12. A biological gas sensor according to claim 11, wherein said metal is selected from the group consisting of copper, silver, cobalt, nickel, iron, manganese, and molybdenum.

13. A biological gas sensor comprising:
a sensor which has in the sensitive part thereof a bicarbonate buffer solution held by a first gas permeable membrane and detects a carbon dioxide partial pressure based on the hydrogen ion concentration of the bicarbonate buffer solution, wherein said gas permeable membrane contains powder of a metal or a compound thereof capable of reacting with hydrogen sulfide.

14. A biological gas sensor according to claim 13, wherein said metal is selected from the group consisting of copper, silver, cobalt, nickel, iron, manganese, and molybdenum.

15. A biological gas sensor comprising:
a sensor which has in the sensitive part thereof a bicarbonate buffer solution held by a first gas permeable membrane and detects a carbon dioxide partial pressure based on the hydrogen ion concentration of the bicarbonate buffer solution;
a liquid holding part which has in the inside thereof the sensitive part of said sensor and at least a part of the inner wall of said holding part is made of a second gas permeable membrane; and
an aqueous alkaline solution which is contained in said liquid holding part and is substantially isotonic with said bicarbonate buffer solution.

16. A biological gas sensor according to claim 15, wherein said gas sensor has a means for allowing carbon dioxide gas into the bicarbonate buffer solution in the sensitive part thereof while preventing hydrogen sulfide or compound gases thereof from reaching the bicarbonate buffer solution.

17. A biological gas sensor according to claim 16, wherein said means is said gas permeable membrane of the sensitive part which contains powder of a metal or a compound thereof capable of reacting with hydrogen sulfide.

* * * * *